United States Patent [19]

Wagner

[11] 4,294,830
[45] Oct. 13, 1981

[54] {[[4-AZIDO-5-(ETHOXYETHYL)-6-PHENYL-2-PYRIMIDINYL]AMINO]CARBONYL}GLYCINE AND ESTERS THEREOF

[75] Inventor: Hans A. Wagner, Skokie, Ill.

[73] Assignee: G. D. Searle & Co., Skokie, Ill.

[21] Appl. No.: 159,703

[22] Filed: Jun. 16, 1980

[51] Int. Cl.³ .................. A61K 31/505; C07D 239/48
[52] U.S. Cl. .................. 424/251; 544/254; 544/323
[58] Field of Search ............... 544/324, 323, 322, 321, 544/254; 424/251

[56] References Cited

U.S. PATENT DOCUMENTS

| | | | |
|---|---|---|---|
| 3,167,553 | 1/1965 | Wagner | 544/321 |
| 3,214,430 | 10/1965 | Rorig et al. | 544/321 |
| 3,281,408 | 10/1966 | Wagner | 544/321 |
| 3,281,420 | 10/1966 | Wagner | 544/321 |
| 3,412,094 | 11/1968 | Rorig et al. | 544/323 |
| 3,481,932 | 12/1969 | Wagner | 544/323 |
| 4,205,169 | 5/1980 | Wagner | 544/323 |

Primary Examiner—Donald G. Daus
Assistant Examiner—Sharon A. Gibson
Attorney, Agent, or Firm—Joyce R. Niblack; James G. Passe

[57] ABSTRACT

Compounds of the formula

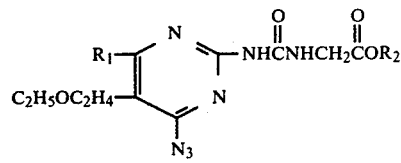

wherein R is phenyl or substituted phenyl, $R_2$ is hydrogen or $C_1$-$C_4$ alkyl and pharmaceutically acceptable salts thereof disclosed. They are useful as antihypertensive agents, substantially devoid of diuretic activity.

5 Claims, No Drawings

{[[4-AZIDO-5-(ETHOXYETHYL)-6-PHENYL-2-PYRIMIDINYL]AMINO]CARBONYL}GLYCINE AND ESTERS THEREOF

BACKGROUND OF THE INVENTION

The etiology of most cases of hypertension is generally unknown. Therefore, the search for effective antihypertensive agents is largely empirical and various classes of agents are currently employed for general antihypertensive therapy.

While a number of effective agents exist, because of the significant, adverse side-effects produced by all effective antihypertensive agents, and because of the need to periodically change agents in given patients, the search for additional antihypertensive agents continues.

The present invention provides one class of new antihypertensive agents.

U.S. Pat. No. 3,412,094 discloses related antihypertensive agents which exhibit diuretic as well as antihypertensive activities. While diuretic therapy is often used in conjunction with antihypertensive therapy, it is not always desirable to administer a diruetic agent as well as an antihypertensive agent. The compounds of the present invention are antihypertensive agents, but surprisingly are substantially devoid of diuretic activity.

SUMMARY

The present invention provides {[4-azido-5-(ethoxyethyl)-6-phenyl-2-pryrimidinyl]amino]carbonyl} glycine and esters thereof represented by the formula

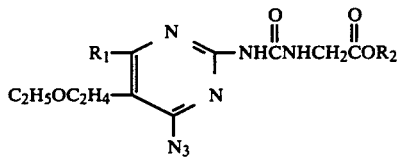

wherein $R_1$ is phenyl or substituted-phenyl; $R_2$ is hydrogen or $C_1$–$C_4$ alkyl; and when $R_2$ is hydrogen the pharmaceutically acceptable salts thereof.

The term "substituted phenyl", as used herein, refers to phenyl containing from one to three substituents selected from the group consisting of lower alkyl or halo.

The term "halo" refers to chloro, fluoro or bromo.

The term "lower alkyl" refers to straight or branched chain alkyl groups containing from 1 to 6 carbon atoms and includes, but is not limited to methyl, ethyl, n-propyl, iso-propyl, n-butyl, sec-butyl, tert-butyl, n-pentyl, 2,2-dimethylbutyl, n-hexyl and the like.

The term "$C_1$ to $C_4$ alkyl" includes straight and branched chain alkyl groups.

The term "lower alkoxy lower alkyl" refers to groups wherein both the alkoxy and alkyl radicals contain from 1 to 6 straight or branched chain carbon atoms, i.e., ethoxymethyl, ethoxyethyl, methoxyethyl, n-propoxymethyl, etc.

The term "pharmaceutically acceptable salts" refers to non-toxic cationic salts of alkali metals, alkaline earth metals, ammonium and substituted ammonium, i.e., sodium, potassium, lithium, magnesium, calcium, maganese etc.

The compounds when $R_2$ is hydrogen are antihypertensive agents at doses of from 30 to 80 mg/kg daily. Compounds where $R_2$ is alkyl are intermediates for compounds where $R_2$ is hydrogen.

DETAILED DESCRIPTION OF PREFERRED EMBODIMENTS

The compounds of this invention when $R_2$ is hydrogen are administered to hypertensive patients orally or parenterally in dosages of from 30 to 80 and preferably 45–60 mg/kg of body weight daily, and most preferably at 50 mg/kg, in divided dosages, preferably every four hours.

The following examples further illustrate the present invention.

EXAMPLE 1

Preparation of N-{[[4-azido-5-(2-ethoxyethyl)-6-phenyl-2-pyrimidinyl]amino]carbonyl}glycine ethyl ester 4-Azido-5-(2-ethoxyethyl)-6-phenyl-2-pyrimidinamine (8.5 g, 0.03 M) (U.S. Pat. No. 3,142,094) was dissolved in pyridine (70 ml) and ethyl isocyanotoacetate (7.7 g, 0.06 M) was added thereto. The resulting solution was allowed to stand at room temperature for 16 hours, then stirred at 75°–80° C. (internal temperature) for 8 hours, and finally allowed to stand at room temperature for another 16 hours. The solution was then poured, with stirring, into 1.2 liters of cold water containing 100 ml of acetic acid. The resulting solid was filtered, washed with water, and dissolved in 1.4 l of diethyl ether. The ether solution was washed 3 times with water, dried over sodium sulfate, filtered, treated with activated charcoal, filtered and concentrated to 300 ml whereupon the product crystallized spontaneously at room temperature to yield 6.7 g of product, m.p. 129.5°–130° C.

Analysis Calc'd. for $C_{19}H_{23}N_7O_4$: C,55.19; H,5.61; N,23.72; Found: C,55.04; H,5.73; N,23.30.

EXAMPLE 2

Preparation of N-{[[4-azido-5-(2-ethoxyethyl)-6-phenyl-2-pyrimidinyl]amino]carbonyl}glycine N-{[[4-Azido-5-(2-ethoxyethyl)-6-phenyl-2-pyrimidinyl]amino]carbonyl}glycine ethyl ester (4.1 g, 0.01 M) was suspended in methanol (40 ml and potassium bicarbonate (1.52 g, 0.01 M+10% excess) in water (10 ml) was added. On heating, a clear, colorless solution was obtained. The solution was maintained at bare reflux for 3 hours and upon cooling, a white, crystalline solid formed. The reaction was poured into 400 ml of cold water with stirring and the white crystalline solid was allowed to settle, filtered, washed with cold water and dried to yield crude product, m.p. 160° C. The basic filtrate was carefully adjusted to pH 4 with dilute hydrochloric acid whereupon a white precipitate formed. The precipitate was allowed to settle, thoroughly washed with water and dried in vacuo under a nitrogen atmosphere at 40° C. The product was recrystallized from methanol, m.p. 175°–176° C.

Analysis Calcd. for $C_{17}H_{19}N_7)_4$: C,52.98; H,4.97; N,25.44. Found: C,52.95; H,4.90; N,25.52.

I claim:

1. A compound of the formula

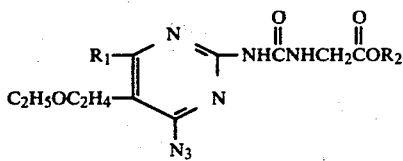

wherein $R_1$ is phenyl or substituted phenyl wherein the substituents are from one to three selected from lower alkyl, chloro, bromo, or fluoro; $R_2$ is hydrogen or $C_1$–$C_4$ alkyl; and when $R_2$ is hydrogen, a pharmaceutically acceptable salt thereof.

2. A compound of claim 1 wherein $R_1$ is phenyl.

3. A compound of claim 2: N-{[[4-azido-5-(2-ethoxyethyl)-6-phenyl-2-pyridiminyl]amino]carbonyl}glycine or a pharmaceutically acceptable salt thereof.

4. A compound of claim 2: N-{[[4-azido-5-(2-ethoxyethyl)-6-phenyl-2-pyrimidinyl]amino]-carbonyl}glycine ethyl ester.

5. A pharmaceutical composition comprising a therapeutically effective amount of a compound of claim 1 and a pharmaceutically acceptable carrier or diluent.

* * * * *